United States Patent
Henning

(10) Patent No.: US 7,550,446 B2
(45) Date of Patent: Jun. 23, 2009

(54) HIGHLY BRANCHED, UNSUBSTITUTED OR LOW-SUBSTITUTED STARCH PRODUCTS, DIALYSIS SOLUTION AND PLASMA EXPANDER CONTAINING THE SAME, AND THE USE THEREOF

(75) Inventor: Klaus Henning, Usingen (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 167 days.

(21) Appl. No.: 10/524,424

(22) PCT Filed: Jul. 30, 2003

(86) PCT No.: PCT/EP03/08411

§ 371 (c)(1),
(2), (4) Date: Jul. 22, 2005

(87) PCT Pub. No.: WO2004/022602

PCT Pub. Date: Mar. 18, 2004

(65) Prior Publication Data

US 2006/0032400 A1 Feb. 16, 2006

(30) Foreign Application Priority Data

Aug. 16, 2002 (DE) ................. 102 37 442

(51) Int. Cl.
*A61K 31/718* (2006.01)
*C08B 31/12* (2006.01)
*C08B 30/00* (2006.01)

(52) U.S. Cl. ......................... 514/60; 536/111

(58) Field of Classification Search ................. None
See application file for complete search history.

(56) References Cited

U.S. PATENT DOCUMENTS 4,454,161 A 6/1984 Okada et al.
5,218,108 A 6/1993 Sommermeyer et al.
6,284,140 B1 9/2001 Sommermeyer et al.
2002/0065410 A1 5/2002 Antrim
2004/0157207 A1 8/2004 Sommermeyer

FOREIGN PATENT DOCUMENTS

| DE | 10141099.9 | * 7/2002 |
|----|------------|----------|
| EP | 0 402 724 | 12/1990 |
| EP | 0 418 945 | 3/1991 |
| EP | 0 602 585 | 6/1994 |
| EP | 1 075 839 | 2/2001 |
| GB | 2 342 656 | 4/2000 |
| JP | 2001/294601 | 10/2001 |
| WO | WO-00/18893 | 4/2000 |
| WO | WO-00/33851 | 6/2000 |
| WO | WO-00/66633 | 11/2000 |
| WO | WO-03/018639 | 3/2003 |
| WO | WO03/018639 | * 3/2003 |

* cited by examiner

*Primary Examiner*—Shaojia Anna Jiang
*Assistant Examiner*—Eric S Olson
(74) *Attorney, Agent, or Firm*—Connolly Bove Lodge & Hutz LLP

(57) ABSTRACT

Known hydroxyethylated and -propylated starch types for use as colloid osmotic agent in peritoneal dialysis or as volume replacement composition (plasma expander) have the disadvantage that complete degradation by amylase is not possible owing to the more or less extensive substitution by hydroxyethyl or hydroxypropyl groups. As a consequence thereof, residual fragments remain in the body and are eliminated only very slowly or are stored in various organs/tissues, especially with relatively high and/or long-term dosage. These disadvantageous properties can be very substantially avoided according to the invention with a highly branched, unsubstituted or low-substituted starch product, i.e. with a starch which has a significantly higher degree of branching than amylopectin, and has the degree of α-1,6 branching of glycogen, or exceeds the latter and—if substituted—has a degree of substitution MS of only up to 0.3.

21 Claims, No Drawings

HIGHLY BRANCHED, UNSUBSTITUTED OR LOW-SUBSTITUTED STARCH PRODUCTS, DIALYSIS SOLUTION AND PLASMA EXPANDER CONTAINING THE SAME, AND THE USE THEREOF

Highly branched, unsubstituted or low-substituted starch products, dialysis solution and plasma expander containing the same, and the use thereof.

The present invention relates to highly branched, unsubstituted or low-substituted starch products which are suitable in particular for use as colloid osmotic agent in peritoneal dialysis and as volume replacement composition (plasma expander).

The osmotic agent mainly employed to date in peritoneal dialysis has been glucose. This has proved suitable in particular for short-term intermittent use (residence time about 2 to 3 hours), is non-toxic, is very compatible with the other ingredients of the dialysis solution and is steam-sterilizable under nonalkaline conditions. In addition, glucose is relatively low-cost. Nevertheless, glucose is not an ideal agent because unwanted side effects may occur during a peritoneal dialysis. Thus, necessarily nonphysiologically low pH values and hyperosmolar solutions lead to irritation. Because reabsorption into the blood is rapid, high blood glucose and blood lipid levels are set up. The ultrafiltration efficiency can therefore be maintained only over relatively short periods.

Apart from avoiding side effects and excessive stress on the peritoneal membrane (the risk of peritonitis increases when the dialysis solution is frequently changed), it was indicated particularly in continuous ambulatory peritoneal dialysis (also called CAPD hereinafter) to replace glucose by an agent which permits a longer residence time of the dialysis solution in the peritoneal cavity and thus reduces the stress on the patient. In this connection, use was made of the realization that a sufficient ultrafiltration efficiency and depletion ("clearance") of solutions is achieved not solely by setting up an osmotic pressure but also through the so-called colloid osmotic pressure exerted by macromolecules. It was possible in this way to use dialysis solutions also in the isoosmolar or hypoosmolar range.

Employed for this purpose are, inter alia, glucose polymers which are obtained by hydrolyzing unmodified corn starch and have molecular weights of about 20 000 (icodextrin).

The residence times of such dialysis solutions are about 8 to 12 hours. Although macromolecules are also reabsorbed by means of active uptake through the lymphatic system, and then degraded, the degradation products in the form of maltose and glucose oligomers are regarded as non-critical.

A considerable disadvantage of such hydrolyzed starch fractions is, however, regarded as being the limitation on the molecular weight by the decrease in water solubility, which is therefore not in the optimal range for the desired use, as the molecular weight grows. In addition, starch fragments with little or no branching are prone to retrogradation—generally known for the amylose content of starch—and may lead to unwanted precipitations. This applies all the more when amylose-rich starches are chosen as initial basis for the hydrolyzates. In addition, maltodextrin-like starch products are prone under the conditions of autoclaving to form unwanted byproducts which are harmful in some circumstances, such as formaldehyde and aldonic acids.

A further agent which can be employed in principle in the art for producing a colloid osmotic pressure is hydroxyethyl starch (HES) which is effective as oncotic medium.

HES is currently the most up-to-date and most widely used volume replacement composition. Besides different compositions of the finished product, the active substance is employed in diverse variants which differ through their molecular weight and through the degree and pattern of substitution.

Hydroxyethyl starches are distinguished in principle from other volume replacement compositions such as gelatin, dextrans or artificial colloids by being well tolerated, based on the fact that the starting material used for HES is waxy corn starch, a special type of starch which is more than 98% composed of amylopectin which has similarity in its chemical structure with the endogenous reserve substance glycogen. The remaining approximately 2% consists of amylose with little or scarcely any branching.

Like glycogen, amylopectin is composed of glucose units which are linked together in the basic structure via $\alpha$-1,4 linkages and at the branch points via $\alpha$-1,6 linkages. Amylopectin with about 5% $\alpha$-1,6 linkages (at approximately every 20th glucose unit) has, however, distinctly less branching than glycogen with 10 to 16% $\alpha$-1,6 linkages (every 6th to 10th glucose unit). Amylopectin is insoluble in water. If it were soluble, it would be rapidly degraded by endogenous amylases and remain ineffective. Etherification with, for example, ethylene oxide or propylene oxide makes amylopectin water-soluble, with in addition a slowing of degradation by amylase—depending on the degree of substitution (degree of etherification)—thus determining, together with the molecular weight which is set up, the desired duration of action when HES is used for example as volume replacement composition.

A serious disadvantage of all known hydroxyethylated and hydropropylated starch types is thus regarded as being the difficulty or impossibility of complete degradation by amylase through the more or less extensive substitution by hydroxyethyl and hydroxypropyl groups, respectively. As a consequence thereof, residual fragments remain in the body and are eliminated only very slowly or are stored in various organs/tissues such as, for example, spleen, liver and lung. This may have particularly critical effects if the dosage is relatively high and/or long-term. It is assumed that the known side effects such as pain in the sides or itching are attributable thereto. Investigations with HES types in the molecular weight range from 40 000 to 450 000 and degrees of substitution of 0.5 and 0.7 for use in peritoneal dialysis revealed that reabsorbed HES and fragments thereof are stored in the spleen, lung and liver, so that the use of HES as colloid osmotic agent cannot be categorized as without problems. This unwanted storage of HES is attributable to the fact that, because of the high degree of substitution, complete degradation of HES by endogenous amylase is not ensured.

An improvement in terms of the storage problem was provided by an HES type with the specification 130/0.4, whose pattern of substitution has been optimized by a special preparation process so that the content of hydroxyethyl side groups which is relevant for attack by amylase was retained but at the same time the overall degree of substitution was decreased. Although it was possible thereby to reduce markedly the storage of HES residual fragments in organs/tissues, it could not be completely suppressed.

The invention was therefore based on the object of providing an agent which has the advantageous properties of the hydroxyethyl and hydroxypropyl starches known in the art but no longer has the disadvantageous properties of storage of residual fragments in organs and tissues.

It has been found that the object can be achieved with a highly branched, unsubstituted or low-substituted starch product, i.e. with a starch which has a significantly higher degree of branching than amylopectin and has the degree of α-1,6 branching of glycogen, or even exceeds this, and—if substituted—has a degree of substitution MS of only up to 0.3, preferably of from 0.05 to 0.3.

The term MS (molar substitution) means the average number of hydroxyethyl or hydroxypropyl groups per anhydroglucose unit. The MS is normally measured by determining the content of hydroxyethyl or hydroxypropyl groups in a sample and computational allocation to the anhydroglucose units present therein. The MS can also be determined by gas chromatography.

The degree of branching can be determined by a gas chromatographic methylation analysis as mol % of the α-1,4,6-glycosidically linked anhydroglucoses in the polymer. The degree of branching is in every case an average because the starch products of the invention are polydisperse compounds.

The glucose units in starch and glycogen and in the product of the invention are linked via α-1,4 and α-1,6 linkages. The degree of branching means the proportion of α-1,4,6-linked glucose units in mol % of the totality of all anhydroglucoses.

The $C_2/C_6$ ratio expresses the ratio or substitution at C-2 to that at C-6.

The starch products of the invention have a degree of branching of from 8% to 20%, achievable by a transglucosidation step with the aid of branching enzymes. The starting material which can be used for this purpose is in principle any starch, but preferably waxy starches with a high proportion of amylopectin or the amylopectin fraction itself. The degree of branching which is necessary for the use according to the invention of the starch products is in the range from 8% to 20%, expressed as mol % of anhydroglucoses. This means that the starch products which can be used for the purposes of the invention have on average one α-1,6 linkage, and thus a branching point, every 12.5 to 5 glucose units.

Preferred starch products have a degree of branching of more than 10% and up to 20% and in particular from 11 to 18%. A higher degree of branching means a greater solubility of the starch products of the invention and a greater bioavailability of these dissolved starch products in the body.

Particular preference is given to unmodified starch products with a degree of branching of more than 10%, in particular from 11% to 18%.

The starch products of the invention can be prepared by targeted enzymatic assembly using so-called branching or transfer enzymes, where appropriate followed by partial derivatization of free hydroxyl groups with hydroxyethyl or hydroxypropyl groups. Instead of this it is possible to convert a hydroxyethylated or hydroxypropylated starch by enzymatic assembly using so-called branching or transfer enzymes into a starch product of the invention. Obtaining branched starch products enzymatically from wheat starch with a degree of branching of up to 10% is known per se and described for example in WO-A-00/66,633. Suitable branching or transfer enzymes and the obtaining thereof are disclosed in WO-A-00/18,893, U.S. Pat. No. 4,454,161, EP-A-418,945, JP-A-2001/294,601 or U.S. Pat. No. 2002/65,410. This latter publication describes unmodified starch products with degrees of branching of more than 4% and up to 10% or higher.

The enzymatic transglycosilation can be carried out in a manner known per se, for example by incubating waxy corn starch with the appropriate enzymes under mild conditions at pH values between 6 and 8 and temperatures between 25 and 40° C. in aqueous solution.

As for the HES types employed clinically in the art, the average molecular weight ($M_w$) is—depending on the application—preferably in the range from 10 000 to 450 000 and, where appropriate, the $C_2/C_6$ ratio is in the range from 4 to 20. Molecular weights in the range from 10 000 to 200 000, in particular 20 000 to 40 000, are preferred for use in CAPD, and molecular weights in the range from 40 000 to 450 000 are preferred for use as plasma expander.

The molecular weight $M_w$ means for the purposes of this description the weight average molecular weight. This can be determined in a manner known per se by various methods, i.e. by gel permeation chromatography (GPC) or high pressure liquid chromatography (HPLC) in conjunction with light scattering and RI detection.

The $C_2/C_6$ ratio preferred for substituted starches is in the range from 5 to 9. The formation of unwanted byproducts such as, for example, aldonic acids and formaldehyde can be avoided by processes known to the skilled worker for reducing or oxidizing aldehyde groups at the reducing end.

The high degree of branching of the starch products of the invention increases the solubility in water thereof to such an extent that hydroxyethyl or hydroxypropyl substitution can be wholly or substantially dispensed with in order to keep the starch product in solution.

A great advantage is in particular that the average molecular weight can be increased in a suitable manner via the permeability limit of the peritoneum. The characteristic variable which can be used in this case is also the GPC value of the so-called bottom fraction BF90% (molecular weight at 90% of the peak area as a measure of the proportion of smaller molecule fractions). A greater UF efficiency can be achieved by appropriate raising of the molecular weight with, at the same time, a drastically reduced absorption across the peritoneal membrane. At the same time, because of the absence of or only low substitution by hydroxyethyl or hydroxypropyl groups, high molecular weight residual fragments which are produced by degradation by endogenous amylase, and which can no longer be further degraded by amylase and are stored in organs or tissues, no longer occur or now occur to only a slight extent. In addition, because of the great physiological similarity to endogenous glycogen compared with prior art HES types, considerably fewer or no side effects are to be expected. Moreover, the possibility of retrogradation and precipitations associated therewith is avoided because these have been observed only on little or unbranched amylose-like structural constituents which are unsubstituted or only slightly substituted.

Starting from suitable highly branched starch it is possible by processes known in the art to prepare with minimal effort a colloid osmotic agent which is suitable for peritoneal dialysis and which can be combined without difficulty in a manner which is likewise known with various electrolytes, amino acids, lactate, acetate, bicarbonate and the like, and with other osmotically active agents, such as, for example, glucose. It is likewise possible by suitable choice of the molecular weight to obtain a product for use as volume replacement composition whose volume effect is additionally favored by the spatial expansion of a starch product highly branched in this way. It is additionally possible to adjust the residence time in the body through the choice of the molecular weight distribution.

The products of the invention are distinguished by having the advantages known in the art for hydroxyethyl starches employed in volume replacement but no longer having the typical disadvantages thereof. This makes them very interesting in particular for use in peritoneal dialysis. Their advantages are particularly advantageously evident in areas of application where volume replacement compositions must be administered intravenously in a short time in relatively large amounts or, as in the case of sudden loss of hearing for example, over relatively long periods. This is because HES is given directly into the bloodstream in volume replacement, whereas on use in peritoneal dialysis only fractions able to pass through the peritoneum or taken up by the lymphatic route can reach the blood. Whereas, for example, the upper limit for one administration of HES of the specification 130/0.4 is currently 3 g per kg of body weight and day, larger amounts of the products of the invention can be administered without problems.

The products of the invention are additionally distinguished by showing the advantages of known colloid osmotic agents for peritoneal dialysis without having the disadvantages of the formation of harmful byproducts or the tendency to retrogradation.

The products of the invention can be employed through modification of the average molecular weight both in volume replacement and in peritoneal dialysis.

The invention likewise relates to dialysis solutions comprising water, the starch products of the invention and further additions customary for dialysis solutions. Examples of the latter are electrolytes, amino acids, lactate, acetate, bicarbonate and other osmotically active agents such as, for example, glucose.

The starch product of the invention is normally present in the dialysis solutions of the invention in a concentration of from 2 to 10, preferably 4 to 7.5, % by weight based on the dialysis solution.

The invention further relates to volume replacement compositions (plasma expanders) comprising water, the starch products of the invention and further additions customary for plasma expanders. An example of the latter is sodium chloride to produce a physiologically tolerated infusion solution.

The starch product of the invention is normally present in the plasma expanders of the invention in a concentration of from 2 to 12, preferably 4 to 10, % by weight based on the plasma expander.

The invention further relates to the use of the starch products of the invention in dialysis, preferably in peritoneal dialysis.

The invention further relates to the use of the starch products of the invention as plasma expanders.

The effectiveness of the starch product of the invention is now explained in detail by means of the following example.

EXAMPLE

Investigation of the tissue storage after repeated administration

A controlled study was carried out on 48 female rats. Daily infusion of a $^{14}$C-labeled starch product of the invention (average molecular weight Mw 25 500 Da; molar substitution 0.15; degree of branching 12.4 mol %) or $^{14}$C-labeled HES 130/0.4 (average molecular weight Mw 135 600 Da; molar substitution 0.41; degree of branching 6.29 mol %; in each case 1 g per kg of body weight) on 24 consecutive days was followed 2, 10, 22 and 46 days after the last administration by investigation of the liver, lung, spleen and kidney for tissue storage. The results are shown in the following table.

As is evident from the table, a significantly lower storage of the product of the invention (P<0.01) compared with HES 130/0.4 was found in all the tissues investigated. These results clearly demonstrate that the product of the invention leads to a distinctly reduced tissue storage compared with the comparison product.

Measured radioactivity in the investigated tissues (as % of total activity administered)

| Tissue | Starch product | HES 130/0.4 | Starch product | HES 130/0.4 | Starch product | HES 130/0.4 | Starch product | HES 130/0.4 |
|---|---|---|---|---|---|---|---|---|
| | 2 days after last administration | | 10 days after last administration | | 22 days after last administration | | 46 days after last administration | |
| Liver | 0.20 | 1.30 | 0.06 | 0.31 | 0.02 | 0.20 | 0.01 | 0.06 |
| Spleen | 0.01 | 0.06 | 0.01 | 0.04 | 0.00 | 0.02 | 0.00 | 0.02 |
| Lung | 0.02 | 0.08 | 0.01 | 0.04 | 0.01 | 0.03 | 0.00 | 0.03 |
| Kidney | 0.02 | 0.13 | 0.01 | 0.05 | 0.00 | 0.01 | 0.00 | 0.01 |

The invention claimed is:

1. A modified hydroxyethyl- or hydroxypropyl-substituted starch product for clinical use, wherein said hydroxyethyl- or hydroxypropyl-substituted starch product has a degree of branching in the range of from 8 to 10 mol %, a degree of substitution MS of up to 0.3, an average molecular weight ($M_w$) in the range of from 10000 to 450000, with the proviso that said hydroxyethyl- or hydroxypropyl-substituted starch product is not derived from an amylopectin fraction.

2. The modified hydroxyethyl- or hydroxypropyl-substituted starch product of claim 1, wherein said modified hydroxyethyl- or hydroxypropyl-substituted starch product has a degree of substitution MS in the range of from 0.05 to 0.3.

3. The modified hydroxyethyl- or hydroxypropyl-substituted starch product of claim 2, wherein said modified hydroxyethyl- or hydroxypropyl-substituted starch product has a degree of substitution MS in the range of from 0.05 to 0.15.

4. The modified hydroxyethyl- or hydroxypropyl-substituted starch product of claim 1, wherein said modified hydroxyethyl- or hydroxypropyl-substituted starch product has an average molecular weight (Mw) in the range from 10,000 to 40,000.

5. The modified hydroxyethyl- or hydroxypropyl-substituted starch product of claim 1, wherein said modified hydroxyethyl- or hydroxypropyl-substituted starch product has an average molecular weight ($M_w$) in the range from 40~000 to 450,000.

6. The modified hydroxyethyl- or hydroxypropyl-substituted starch product of claim 1, wherein the C2/C6 ratio of said modified hydroxyethyl- or hydroxypropyl-substituted starch product is in the range of from 4 to 20.

7. The modified hydroxyethyl- or hydroxypropyl-substituted starch product of claim 6, wherein said C2/C6 ratio is in the range of from 5 to 9.

8. The modified hydroxyethyl- or hydroxypropyl-substituted starch product of claim 1, wherein said hydroxyethyl- or hydroxypropyl-substituted starch product is hydroxyethylated starch.

9. The modified hydroxyethyl- or hydroxypropyl-substituted starch product of claim 1, wherein the reducing ends of said modified hydroxyethyl- or hydroxypropyl-substituted starch product are inactivated by oxidation or reduction.

10. A dialysis solution comprising water and the modified hydroxyethyl- or hydroxypropyl-substituted starch product of claim 1.

11. A plasma expander comprising water and the modified hydroxyethyl- or, hydroxypropyl-substituted starch product of claim 1.

12. A method of peritoneal dialysis comprising dialyzing with a dialysis solution comprising the modified hydroxyethyl- or hydroxypropyl-substituted starch product of claim 1 as colloid osmotic agent in dialysis.

13. A method for volume replacement comprising administering to a patient in need thereof a plasma expander comprising the modified hydroxyethyl- or hydroxypropyl-substituted starch product of claim 1.

14. A modified unsubstituted starch product for clinical use, wherein said modified unsubstituted starch product has a degree of branching in the range of from 11 to 20 mol % and an average molecular weight ($M_w$) in the range of from 10,000 to 450,000, with the proviso that said unsubstituted starch product is not derived from an amylopectin fraction.

15. The modified unsubstituted starch product of claim 14, wherein said modified unsubstituted starch product has an average molecular weight ($M_w$) in the range from 10,000 to 40,000.

16. The modified unsubstituted starch product of claim 14, wherein said modified unsubstituted starch product has an average molecular weight ($M_w$) in the range from 40,000 to 450,000.

17. The modified unsubstituted starch product of claim 14, wherein the reducing ends of said modified unsubstituted starch product are inactivated by oxidation or reduction.

18. A dialysis solution comprising water and the modified unsubstituted starch product of claim 14.

19. A plasma expander comprising water and the modified unsubstituted starch product of claim 14.

20. A method of peritoneal dialysis comprising dialyzing with a dialysis solution comprising the modified unsubstituted starch product of claim 14 as colloid osmotic agent in dialysis.

21. A method for volume replacement comprising administering to a patient in need thereof a plasma expander comprising the modified unsubstituted starch product of claim 14.

* * * * *